(12) United States Patent
Domokos et al.

(10) Patent No.: US 9,376,325 B2
(45) Date of Patent: Jun. 28, 2016

(54) ZSM-5, ITS PREPARATION AND USE IN ETHYLBENZENE DEALKYLATION

(71) Applicant: SHELL OIL Company, Houston, TX (US)

(72) Inventors: Laszlo Domokos, Amsterdam (NL); Ralph Haswell, Amsterdam (NL); Hong-Xin Li, Lansdale, PA (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/922,328

(22) Filed: Jun. 20, 2013

(65) Prior Publication Data

US 2013/0281757 A1 Oct. 24, 2013

Related U.S. Application Data

(62) Division of application No. 12/677,009, filed as application No. PCT/EP2008/061967 on Sep. 10, 2008, now Pat. No. 8,574,542.

(60) Provisional application No. 60/971,130, filed on Sep. 10, 2007, provisional application No. 61/080,823, filed on Jul. 15, 2008.

(51) Int. Cl.

| C07C 4/18 | (2006.01) |
|---|---|
| C01B 39/40 | (2006.01) |
| B01J 29/40 | (2006.01) |
| B01J 29/44 | (2006.01) |
| B01J 37/00 | (2006.01) |
| C01B 39/38 | (2006.01) |
| B01J 29/46 | (2006.01) |

(52) U.S. Cl.
CPC ............... *C01B 39/40* (2013.01); *B01J 29/40* (2013.01); *B01J 29/405* (2013.01); *B01J 29/44* (2013.01); *B01J 29/46* (2013.01); *B01J 37/0009* (2013.01); *C01B 39/38* (2013.01); *C07C 4/18* (2013.01); *B01J 2229/20* (2013.01); *B01J 2229/42* (2013.01); *C07C 2529/40* (2013.01); *C07C 2529/42* (2013.01); *C07C 2529/44* (2013.01); *C07C 2529/46* (2013.01); *C07C 2529/48* (2013.01); *Y02P 20/52* (2015.11)

(58) Field of Classification Search
CPC ...... C01B 39/38; C01B 39/026; C01B 39/40; C07C 4/18; C07C 2529/40; C07C 2529/42; C07C 2529/44; C07C 2529/46; C07C 2529/48; B01J 29/40; B01J 29/405; B01J 29/44; B01J 29/46; B01J 2229/16; B01J 2229/32
USPC ...................... 585/488, 489; 423/700; 502/71
See application file for complete search history.

(56) References Cited

U.S. PATENT DOCUMENTS

| 3,702,886 | A | 11/1972 | Argauer et al. | |
|---|---|---|---|---|
| 4,088,605 | A | 5/1978 | Rollmann | |
| 4,511,547 | A | 4/1985 | Iwayama et al. | |
| 5,004,855 | A * | 4/1991 | Tada et al. | 585/489 |
| 5,242,676 | A | 9/1993 | Apelian et al. | |
| 6,831,203 | B1 * | 12/2004 | Mohr et al. | 585/419 |
| 6,949,181 | B2 | 9/2005 | Remans et al. | |
| 2010/0217057 | A1 * | 8/2010 | Domokos et al. | 585/488 |
| 2010/0249479 | A1 * | 9/2010 | Berg-Slot et al. | 585/489 |

FOREIGN PATENT DOCUMENTS

WO 2006056876 6/2006

OTHER PUBLICATIONS

Kirk-Othmer Encyclopedia of Chemical Technology, 4th Ed., vol. 13; pp. 1071-1078.
Friel, J. et al.; "X-ray Mapping in Electron-Beam Instruments"; Microscopy and Microanalysis; pp. 1-24; Dec. 2006.

* cited by examiner

*Primary Examiner* — David M Brunsman
(74) *Attorney, Agent, or Firm* — Charles W. Stewart (57) ABSTRACT

A new configuration of ZSM-5 is provided whereby the crystals have a higher average silica to alumina ratio at the edges of each crystallite than in the center as determined from a narrow slit line scan profile obtained from SEM/EDX or TEM/EDX elemental analysis. Such ZSM-5 crystals are obtained by a preparation process using L-tartaric acid. The new configuration ZSM-5 provides significantly reduced xylene losses in ethylbenzene dealkylation, especially when combined with silica as binder, and one or more hydrogenation metals selected from platinum, tin, lead, silver, copper, and nickel.

9 Claims, 3 Drawing Sheets

ZSM-5, ITS PREPARATION AND USE IN ETHYLBENZENE DEALKYLATION

This application is a divisional application of Ser. No. 12/677,009, filed May 4, 2010, which application was the National Stage of International Application PCT/EP08/61967, filed Sep. 10, 2008, which claims the benefit of U.S. Provisional Application No. 60/971,130, filed Sep. 10, 2007 and claims the benefit of U.S. Provisional Application No. 61/080,823, filed Jul. 15, 2008

FIELD OF THE INVENTION

The present invention relates to ZSM-5, its preparation, catalyst composition containing it, and its use in ethylbenzene dealkylation.

BACKGROUND OF THE INVENTION

Ethylbenzene is one of the aromatic hydrocarbons that is obtained from naphtha pyrolysis or in reformate. Reformate is an aromatic product given by the catalysed conversion of straight-run hydrocarbons boiling in the 70 to 190° C. range, such as straight-run naphtha. Such hydrocarbons are themselves obtained by fractionation or distillation of crude petroleum oil, their composition varying depending on the source of the crude oil, but generally having a low aromatics content. On conversion to reformate, the aromatics content is considerably increased and the resulting hydrocarbon mixture becomes highly desirable as a source of valuable chemicals intermediates and as a component for gasoline. The principle components are a group of aromatics often referred to as BTX: benzene, toluene, and the xylenes, including ethylbenzene. Other components may be present such as their hydrogenated homologues, e.g. cyclohexane.

Of the BTX group the most valuable components are benzene and the xylenes, and therefore BTX is often subjected to processing to increase the proportion of those two aromatics: hydrodealkylation of toluene to benzene and toluene disproportionation to benzene and xylenes. Within the xylenes, para-xylene is the most useful commodity and xylene isomerisation or transalkylation processes have been developed to increase the proportion of para-xylene.

A further process that the gasoline producer can utilize is the hydrodealkylation of ethylbenzene to benzene.

Generally, the gasoline producer will isolate BTX from the reformate stream, and then subject the BTX stream to xylene isomerisation with the aim of maximising the para-xylene component. Xylene isomerisation is a catalytic process; some catalysts used in this process have the ability not just to isomerise xylenes but also simultaneously to dealkylate the ethylbenzene component. Normally the para-xylene is then separated out to leave benzene, toluene (unless toluene conversion processes have already been applied) and the remaining mixed xylenes, including ethylbenzene. This BTX stream can either be converted by transalkylation to increase the yield of xylenes by contacting with a heavier hydrocarbon stream or can be converted by dealkylation to eliminate selectively ethylbenzene and to increase the yield of benzene, while allowing the xylenes to reach equilibrium concentrations. The latter process is the subject of the present invention.

In ethylbenzene dealkylation at this latter stage of BTX treatment, it is a primary concern to ensure not just a high degree of conversion to benzene but also to avoid xylene loss. Xylenes may typically be lost due to transalkylation, e.g. between benzene and xylene to give toluene, or by addition of hydrogen to form, for example, alkenes or alkanes.

It is therefore the aim of the present invention to provide catalytic materials that will convert ethylbenzene to benzene with a reduced xylene loss.

For the conversion of BTX streams to increase the proportion of closely configured molecules, a wide range of proposals utilizing zeolitic catalysts have been made. One common zeolite group utilized in the dealkylation of ethylbenzene is the MFI zeolites and in particular ZSM-5. The ZSM-5 zeolite is well known and documented in the art.

Many preparation routes have been proposed that provide active MFI zeolites, including ZSM-5, see for example U.S. Pat. No. 3,702,886.

U.S. Pat. No. 4,511,547 proposes a general preparation route for the production of crystalline aluminosilicate zeolites which comprises stirring, whilst heating, an aqueous reaction mixture containing a silica source, an alumina source, an alkali source and an organic carboxylic acid which does not contain an aromatic ring, suitably an organic carboxylic acid having from 1 to 12 carbon atoms. The examples of U.S. Pat. No. 4,511,547 utilise tartaric acid and, from the XRD pattern provided, produce ZSM-5 type zeolite.

Tartaric acid has two chiral centres and exists in four main enantiomeric forms: racemic, meso, levorotatory and dextrorotatory. The racemic form (DL-tartaric acid) is readily available and produced commercially in Europe, South Africa and Japan while the dextrorotatory form (L-tartaric acid) is the commercial product in the USA approved by the FDA for use in the food and pharmaceutical industries (see the Kirk-Othmer Encyclopedia of Chemical Technology, $4^{th}$ Edition, Volume 13, pages 1071 to 1078). U.S. Pat. No. 4,511,547 is silent as to the form of tartaric acid utilized but the examples come from Japanese-originating research and it is reasonable to conclude that the racemic form of tartaric acid was used.

SUMMARY OF THE INVENTION

We have now found that a catalyst composition containing a particular configuration of ZSM-5 crystals can provide significantly reduced xylene losses in ethylbenzene dealkylation. The ZSM-5 configuration is obtained when utilising only one isomer of tartaric acid in the zeolite synthesis. The new configuration of ZSM-5 is detectable at the crystalline level and we have developed a new method of analysing specific X-ray spectroscopy data to enable selection of the higher performing ZSM-5 crystals by pinpointing this new configuration.

Accordingly the present invention provides ZSM-5 crystals which have a higher average SAR at the edge of each crystallite than at the centre, as determined via SEM/EDX or TEM/EDX elemental analysis.

Also provided by the present invention is a process for the preparation of ZSM-5 crystals of the present invention which comprises synthesizing the crystals from an aqueous reaction mixture comprising an alumina source, a silica source, an alkali source, and L-tartaric acid, or a water-soluble salt thereof.

Additionally provided by the present invention is a process for selecting ZSM-5 crystals having a high selectivity for ethylbenzene dealkylation, which comprises subjecting ZSM-5 crystals to SEM/EDX or TEM/EDX elemental analysis, calculating the SAR across the crystals and selecting those crystals which exhibit a U- or dish-shaped narrow slit line scan profile on a graph of SAR across the crystallite from edge to edge, wherein the average SAR is higher at the edge of the crystallite than at the centre.

A catalyst composition which comprises ZSM-5 crystals of the present invention is further provided, and also an ethylbenzene dealkylation process which comprises contacting, in the presence of hydrogen, a feedstock which comprises ethylbenzene with a catalyst composition of the present invention.

DETAILED DESCRIPTION OF THE INVENTION

The ZSM-5 crystals of the present invention have been found to provide much reduced xylene losses compared with those having no differentiation in SAR from crystal edge to centre, and those prepared utilising DL-tartaric acid. Since the reduction of xylene losses is an indication of increased selectivity of reaction, there is accordingly an unexpected correlation between the intraparticle distribution of aluminium in a ZSM-5 type zeolite and the selectivity of a catalyst based on this zeolite in the dealkylation reaction of ethylbenzene.

We have found that from the elemental maps produced from the two dimensional recording of the energy dispersive X-ray spectroscopy (EDX) coupled with transmission or scanning electron microscopy (TEM or SEM, respectively), it is possible to generate a consistent high-resolution one dimensional profile for the distribution of specific elements. We have developed a new method for the generation of "narrow slit" profiles, where the lateral resolution of the profiling is kept in the range of 50 nm; this can be slightly improved if necessary. This high-resolution distribution profile, e.g. across a solid particle, can be used for the display of amounts of elements of components against a direction, from e.g. the edge to the centre of the particle. The elemental information (including the obtained profiles) then allows the calculation of e.g. ratios of elements or components, often used in the characterization of chemical substances, in a similar fashion.

In zeolite characterization the ratio of silica to alumina ($SiO_2/Al_2O_3$ herein 'SAR') is an important parameter. This parameter is inversely related to the acid site density associated with the presence of aluminium in the framework of a crystalline aluminosilicate zeolite. In high-resolution micrographs of SEM/EDX or TEM/EDX, the available high data-density allows a more detailed analysis of the zeolite crystallites. This is to say that not only an average chemical composition can be obtained, but also the variations in the local chemical composition to a very high detail with ~50 nm lateral resolution.

Conventionally SAR is determined for crystalline aluminosilicate zeolitic materials by bulk elemental analysis. As noted above in the present invention the SAR at crystalline level is determined utilising elemental maps produced from energy dispersive X-ray spectroscopy (EDX) coupled with transmission electron microscopy (TEM) or scanning electron microscopy (SEM). EDX, TEM and SEM are documented techniques, see Chapter 9, Scanning Electron Microscopy and X-ray Microanalysis, Plenum Press, 1992, and Surface Characterization: A User's Sourcebook, edited by D. Brune, et al., Wiley-VCH Verlag GmbH, November 1997, ISBN 3-527-28843-0, particularly pages 109 to 288.

The chemical composition of samples studied is often determined in scanning or transmission electron microscopy. This determination is achieved by detecting the X-rays that are produced as a result of in-elastic collisions between the primary electrons from the SEM and the electrons in the sample itself. Each element produces X-rays with characteristic energies. By measuring the energies of the X-rays emitted from the sample, it is possible to determine the elements present in the sample.

The strong interaction between electrons and solids means that the minimum lateral resolution possible is around 1-5 microns, depending on the initial energy of the primary electrons. As well as a qualitative examination, it is also possible to quantify the results by comparing the number of X-rays detected. This requires a number of corrections relating to the differences in ionization cross-section for the elements and energy dependent absorption of the X-rays. The details of the correction method is not considered here but in general the accuracy of this analysis method is 10% or better for samples with an atomic number greater than 10. In the case of elements with an atomic number less than 10, the accuracy can be significantly worse.

The chemical information can be measured with the beam stationary or as it is scanned. In the stationary mode it is possible to count for a few hundred seconds which will give a spectra with a good signal to noise ratio and can be used for accurate quantification. In the scanning mode, the data is more qualitative but it is possible to build up a picture of the spatial distribution of the various elements in the sample. Such scans are usually referred to as X-ray maps.

In high-resolution micrographs of SEM/EDX or TEM/EDX the high data density available allows further processing of the information. It allows one to 'look inside' an individual zeolite crystallite, and to obtain local information about the variations in the chemical composition within the particle or the crystallite itself.

Next to the standard statistical methods applied to deal with large amounts of data, we herein propose a new method that allows averaging without losing the lateral resolution of the original X-ray map.

The SEM/EDX (or TEM/EDX) maps are obtained as follows. At small magnification, a suitable region of the sample is selected where some crystallites are standing free from the rest of the sample. A freestanding crystallite is selected randomly. The magnification is then increased so that the crystallite fills at least 75% of the viewfinder of the microscope. This is done to "maximize" the possible information to be gathered from the elemental analysis per image taken, and to increase the number of analysis points across the zeolite crystal.

The zeolite crystallite is then aligned so that the longest edge of the crystal is parallel to the longer edge of the viewfinder (or the picture that will be taken). As ZSM-5 crystallites tend to have an elongated (often coffin shaped) form, it frequently occurs that part of the crystallite is left out of the image whilst trying to increase the magnification to occupy at least 75% of the visible area. This is to say that in almost all cases part of the zeolite crystal has to be left out from the final image. It is important that one end of the crystallite is still visible in the viewfinder of the instrument. If the alignment and the magnification are carried out correctly, the above described process results in a picture where both the two sides along the longest axis, and one end of the crystallite are visible in the final elemental map.

An EDX grid of sufficiently high resolution is placed on the image (typically dictated by the instrument), and an EDX elemental map is obtained which provides at each location or point the amount of each element at that point—a spacial composition map. From the elemental map, the SAR values at each point are calculated and a SAR map obtained. We will refer to both the obtained elemental and the calculated SAR map as an X-ray map, or analysis (mapping) matrix below reflecting its numerical nature.

The "narrow slit" line scan profiles are calculated from the obtained X-ray SAR mapping data. The orientation of the maps is identical, so the "base" of the maps, where the zeolite crystal extends beyond the map, is at the identical edge of all pictures. Furthermore, since extra care is taken to align the crystallites along the measurement area, the orientation of the zeolite crystal is also parallel to the obtained analysis matrix. The realigned mapping matrices (obtained by rotating clock- or counterclockwise) are averaged in each column over a selected range of rows aiming at the middle of the crystal stem, away from the base, and from the tip as well. Approximately 30 rows are selected, and averaged for each lateral point (column).

The X-ray maps where the crystal does not touch any of the sides are handled differently. In this case, the middle section of the crystal is selected, averaging also approximately 30 lines.

By obtaining the 'vertical' averages while moving across the crystal from one side to the other, the averages provide a narrow slit overview of the crystallite. It does not compromise the lateral resolution across the crystallite, but still averages the local possible imperfections with the neighbouring map points. It is important to keep in mind that the averaging occurs in the direction where structural similarity (e.g. similar SAR) is expected, and not in the direction where the variations in the composition are claimed. The obtained profiles therefore are more sensitive to structural variations in the aluminum and silicon distribution from edge to centre, while it is less sensitive to imperfections in the shape of the crystallites along the long axis.

One has to realize the very high resolution of these line scans. The cell size is ~50 nm that provides excellent resolution at the scale of individual crystallites, in the range of 1-5 µm—far beyond the normal line scan resolution obtained in e.g. extrudate analysis. It has to be remembered that this is not the native resolution of the maps, as the data is first grouped due to various reasons. The main reason is that the grouping increases the signal to noise ratio in the X-ray maps, and it allows a far better detection of the elements present in only small quantities (close to the detection limit of the equipment).

Figure 3:
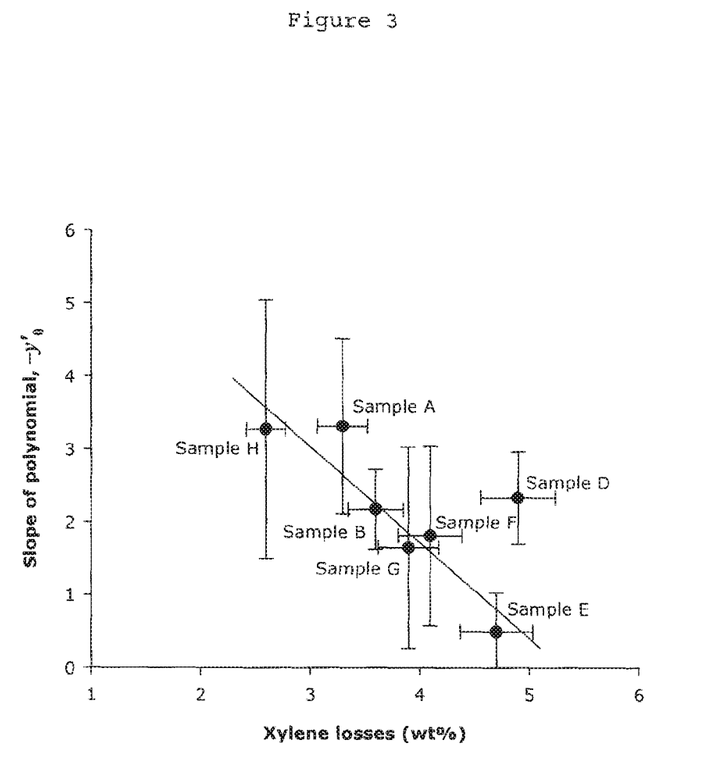
FIG. 3 are plots of the slopes of the narrow slit scan profiles of crystallites of various zeolite samples against the xylene losses obtained in testing of the catalytic properties of the zeolite.

The obtained line scan profiles can be compared by fitting a second order polynomial to the available experimental data in the range between the two maxima at the edge of the profiles. The slope of the polynomial $y=a_2x^2+a_1x+a_0$ is determined by derivation according to the conventions as $y'=2a_2x+a_1$. The slope is determined at $x=0$, so it is $y'_0=a_1$. As $a_1$ tends to have a negative value, $-y'_0=-a_1$ is shown in Figure 3 herewith.

This value can be correlated with e.g. various performance parameters measured with catalysts made from the zeolites studied with SEM/EDX or TEM/EDX.

In the present invention, ZSM-5 crystals are provided that have a higher local average SAR at the edge of each crystallite than at the centre as determined from a narrow slit line scan profile obtained from SEM/EDX or TEM/EDX elemental analysis as hereinbefore described. Most suitably the ratio of the average SAR at the edge of each crystallite to the average SAR at the centre of the crystallite is at least 1.15, preferably at least 1.25. The ratio is most suitably at most 3, preferably at most 2.

The average SAR at the centre of the crystallite is the average of the 3 middle SAR values of the narrow slit line scan profile, i.e. the average of the middle value and the values either side of the middle value. The average SAR at the edge of each crystallite is obtained by calculating the average of the SAR at the three outermost points at each end of the narrow slit line scan profile and then calculating the average of the two values obtained.

Where the data is converted to a second order polynomial, then the slope fitted to the SAR values between the two edge SAR maxima, expressed as $-y'_0$, is most suitably at least 2, and preferably at least 3. The slope is most suitably at most 6, and preferably at most 4.

The preparation of the advantageous ZSM-5 crystals of the present invention is via the process of U.S. Pat. No. 4,511,547, the contents of which are hereby incorporated by reference, with the amounts of silica, alumina, alkali, and tartaric acid adapted as necessary to produce ZSM-5. This adaptation would be within the normal knowledge and skill of the skilled person in the art. As noted in U.S. Pat. No. 4,511,547, the reaction mixture is desirably kept in a homogeneous state during crystallization by suitable agitation of the reaction mixture.

L-tartaric acid, or a water-soluble salt thereof, is used in the preparation process of the present invention. This L-isomer is the dextrorotatory form and is variously named (2R,3R)-(+)-tartaric acid, or (2R,3R)-2,3-dihydroxybutanedioic acid, or (R-R*,R*)-tartaric acid, depending on the naming convention used.

We have found an unexpected correlation between the above-described slope of the silica to alumina ratios in a crystallite ZSM-5 zeolite (MFI) structure and the xylene losses in ethylbenzene (EB) dealkylation process particularly when incorporated into a silica-bound catalyst, which contains 40 wt % of the above mentioned ZSM-5 zeolite in the carrier.

Silica is preferably used as the binder in the catalyst composition of the present invention and may be a naturally occurring silica or may be in the form of a gelatinous precipitate, sol or gel. The form of silica is not limited and the silica may be in any of its various forms: crystalline silica, vitreous silica or amorphous silica. The term amorphous silica encompasses the wet process types, including precipitated silicas and silica gels, of pyrogenic or fumed silicas. Silica sols or colloidal silicas are non-settling dispersions of amorphous silicas in a liquid, usually water, typically stabilised by anions, cations, or non-ionic materials.

The silica binder is preferably a mixture of two silica types, most preferably a mixture of a powder form silica and a silica sol. Conveniently powder form silica has a surface area in the range of from 50 to 1000 m$^2$/g; and a mean particle size in the range of from 2 nm to 200 µm, preferably in the range from 2 to 100 µm, more preferably 2-60 µm especially 2-10 µm as measured by ASTM C 690-1992 or ISO 8130-1. A very suitable powder form silica material is Sipernat 50, a white silica powder having predominately spherical particles, available from Degussa (Sipernat is a trade name). A very suitable silica sol is that sold under the trade name of Bindzil by Eka Chemicals. Where the mixture comprises a powder form silica and a silica sol, then the two components may be present in a weight ratio of powder form to sol in the range of from 1:1 to 10:1, preferably from 2:1 to 5:1, more preferably from 2:1 to 3:1. The binder may also consist essentially of just the powder form silica.

Where a powder form of silica is used the binder in the catalyst composition of the present invention, preferably a small particulate form is utilised, which has a mean particle size in the range of from 2 to 10 µm as measured by ASTM C 690-1992. An additional improvement in carrier strength can be found with such materials. A very suitable small particulate form is that available from Degussa under the trade name Sipernat 500LS.

The silica component used may be pure silica and not as a component in another inorganic oxide. For certain embodiments, the silica and indeed the carrier, is essentially free of any other inorganic oxide binder material, and especially is free of alumina. Optionally, at most only a maximum of 2 wt % alumina, based on the total carrier, is present.

For certain embodiments a surface modification treatment may be performed. For such embodiments, the presence of alumina can detrimentally affect the physical integrity of the carrier and so is less preferred.

The ZSM-5 zeolite can exist in various forms depending on the ion present at the cation sites in the zeolite structure. Generally the available forms contain an alkali metal ion, an alkaline earth metal ion, or a hydrogen or hydrogen precursor ion at the cation site. In the catalyst composition of the present invention, the zeolite is present in the form containing hydrogen or hydrogen precursor; this form is commonly known as the $H^+$ form. The zeolite may be used either in a template-free or a template-containing form.

The bulk overall SAR, measured by bulk (rather than crystalline level) elemental analysis, of the ZSM-5 is preferably at least 25, most preferably at least 30, and is preferably at most 100, most preferably at most 90, especially at most 50.

The ZSM-5 zeolite can exist in a number of particle size ranges. Suitably the zeolite has a primary particle diameter in the range of from 20 nm to 10 µm. Useful catalysts have been prepared using a large crystal size ZSM-5 zeolite having an average crystallite size in the range of from 1 to 10 µm, and also using a small particle size ZSM-5 having a primary particle diameter below 200 nm. Generally, in terms of particle size distributions, the ZSM-5 may have a particle size distribution in which the diameter of 50% of the particles, D(v, 0.5), is greater than 2 µm and that of 90% of the particles, D(v, 0.9), is less than 30 µm.

The zeolite is an important factor in the activity and selectivity properties shown by the catalyst composition of the invention. There is a balance between the activity and selectivity desired which may result in a different optimum zeolite content in the carrier depending on the SAR of the zeolite used. Generally a higher zeolite content may in some cases be advantageous to produce a higher activity from the catalyst composition, while a lower zeolite content may provide a higher selectivity.

While this balance may cause a different optimum depending on the conditions utilized in the ethylbenzene dealkylation process, generally it is preferred to minimize the amount of zeolite used in the catalyst carrier, since a higher amount of zeolite may negatively affect the physical properties of the catalyst carrier such as lowering its strength. It is generally preferred that the carrier is composed of in the range of from 30 to 80 wt %, most preferably from 50 to 70 wt %, silica and in the range of from 20 to 70 wt %, most preferably from 30 to 50 wt %, zeolite.

A very suitable catalyst carrier for the present invention contains the ZSM-5 crystals of the present invention in an amount in the range of from 20 to 50 wt %, especially 25 to 40 wt %.

Preferably there is no other component than binder, preferably silica, and ZSM-5 zeolite in the carrier. However it is possible to include up to 10 wt % of other components whilst still obtaining the benefits of the present invention. Such other components may be selected from other refractory inorganic oxide binder materials and other zeolites. Other binder materials may be alumina, and magnesia. Examples of other zeolites are 8, 10, or 12-membered ring zeolites, for example mordenite, and zeolite beta, and acidic mesoporous materials such as the MCM-series of zeolites, e.g. MCM-22 and MCM-41.

The carrier is conveniently a shaped carrier and may be treated to enhance the activity of the zeolite component. It may be advantageous to perform a surface modification, such as is described in U.S. Pat. No. B2-6,949,181.

Modification of the molecular sieve reduces the mole percentage of alumina which basically implies that the number of acid sites is reduced. This can be achieved in various ways. A first way is applying a coating of a low acidity inorganic refractory oxide onto the surface of the crystallites of the molecular sieve.

Another very useful way of modifying the molecular sieve is by subjecting it to a dealumination treatment. In general, dealumination of the crystallites of a molecular sieve refers to a treatment, whereby aluminium atoms are either withdrawn from the molecular sieve framework leaving a defect or are withdrawn and replaced by other atoms, such as silicon, titanium, boron, germanium, or zirconium.

In U.S. Pat. No. 5,242,676, a very suitable method for the dealumination of the surface of zeolite crystallites is disclosed. Another method for obtaining a zeolite having a dealuminated outer surface is disclosed in U.S. Pat. No. 4,088,605.

Of the (surface) dealumination methods described above, the method involving the treatment with a hexafluorosilicate, most suitably ammoniumhexa-fluoro silicate (AHS) as described in U.S. Pat. No. B2-6,949,181, can be expected to offer additional advantage.

The catalyst composition of the invention most suitably also contains a hydrogenation metal selected from platinum, tin, lead, silver, copper, and nickel. Preferably the metal component is platinum. More preferably an additional metal component selected from tin, lead, copper, nickel, and silver, is present.

The platinum component is preferably present in an amount in the range of from 0.001 to 0.1 wt %, based on total catalyst. Preferably the additional metal component is less than 1 wt %. Most suitably the platinum content is present in an amount in the range of from 0.01 to 0.1 wt %, and preferably from 0.01 to 0.05 wt %. The additional metal component is most suitably present in the range from 0.001 to 0.5 wt %.

An additional metal component of copper, nickel or silver is preferably present in the range of from 0.0001 to 0.1 wt %, based on the total catalyst. If tin or lead is the additional metal component then it is present in an amount in the range of from 0.01 to 0.5 wt %, based on total catalyst, most suitably present in an amount in the range of from 0.1 to 0.5, preferably 0.2 to 0.5, wt %.

The catalyst composition of the present invention may be prepared using standard techniques for combining the zeolite, binder such as silica, and optional other carrier components;

shaping; compositing with the metals components; and any subsequent useful process steps such as drying, calcining, and reducing.

The shaping may be into any convenient form such as powders, extrudates, pills and granules. Preference is given to shaping by extrusion. To prepare extrudates, commonly the ZSM-5 zeolite will be combined with the binder, preferably silica, and if necessary a peptizing agent, and mixed to form a dough or thick paste. The peptizing agent may be any material that will change the pH of the mixture sufficiently to induce deagglomeration of the solid particles. Peptising agents are well known and encompass organic and inorganic acids, such as nitric acid, and alkaline materials such as ammonia, ammonium hydroxide, alkali metal hydroxides, preferably sodium hydroxide and potassium hydroxide, alkali earth hydroxides and organic amines, e.g. methylamine and ethylamine. Ammonia is a preferred peptizing agent and may be provided in any suitable form, for example via an ammonia precursor. Examples of ammonia precursors are ammonium hydroxide and urea. It is also possible for the ammonia to be present as part of the silica component, particularly where a silica sol is used, though additional ammonia may still be needed to impart the appropriate pH change.

The amount of ammonia present during extrusion may affect the pore structure of the extrudates which may provide advantageous properties. Suitably the amount of ammonia present during extrusion may be in the range of from 0 to 5 wt % based on total dry mixture, more preferably 0 to 3 wt %, preferably 0-1.9 wt % on dry basis. It is preferable that a calcination step be carried out on the resultant extrudate prior to emplacement of the metal components, this is preferably carried out at temperatures above 500° C. and typically above 600° C.

The metals emplacement onto the formed carrier may be by methods usual in the art. The metals can be deposited onto the carrier materials prior to shaping, but it is preferred to deposit them onto a shaped carrier.

Pore volume impregnation of the metals from a metal salt solution is a very suitable method of metals emplacement onto a shaped carrier. The metal salt solutions may have a pH in the range of from 1 to 12. The platinum salts that may conveniently be used are chloroplatinic acid and ammonium stabilised platinum salts. The additional silver, nickel or copper metal salt will typically be added in the form of water soluble organic or inorganic salt in solution. Examples of suitable salts are nitrates, sulphates, hydroxides and ammonium (amine) complexes. Examples of suitable tin salts that may be utilized are stannous (II) chloride, stannic (IV) chloride, stannous sulphate, and stannous acetate. Examples of suitable lead salts are lead acetate, lead nitrate, and lead sulphate.

Where there is more than one metals component, the metals may be impregnated either sequentially or simultaneously. It is preferable that the metals be added simultaneously. Where simultaneous impregnation is utilised the metal salts used must be compatible and not hinder the deposition of the metals. It may be useful to utilise a complexing agent or chelating agent in a combined bimetallic salt solution to prevent unwanted metals precipitation. Examples of suitable complexing agents are EDTA (ethlyenediaminetetraacetic acid), and derivatives thereof; HEDTA (N-(2-hydroxyethyl) ethylenediamine-N,N',N'-triacetic acid), EGTA (ethylene glycol-bis(2-aminoethylether)-N,N,N',N'-tetraacetic acid), DTPA (diethylene tridiamine pentaacetic acid), and NTA (nitrilotriacetic acid). Where EDTA is used, it is conveniently used in a molar ratio to the additional metal of from 0.1 to 3, especially 1 to 2.

After shaping of the carrier, and also after metals impregnation, the carrier/catalyst composition is suitably dried, and calcined. Drying temperatures are suitably 50 to 200° C.; drying times are suitably from 0.5 to 5 hours. Calcination temperatures are very suitably in the range of from 200 to 800° C., preferably 300 to 600° C. For calcination of the carrier, a relatively short time period is required, for example 0.5 to 3 hours. For calcination of the catalyst composition, it may be necessary to employ controlled temperature ramping at a low rate of heating to ensure the optimum dispersion of the metals: such calcination may require from 5 to 20 hours.

Prior to use, it is necessary to ensure that any hydrogenation metals on the catalyst composition are in metallic (and not oxidic) form. Accordingly, it is useful to subject the composition to reducing conditions, which are, for example, heating in a reducing atmosphere, such as in hydrogen optionally diluted with an inert gas, or mixture of inert gases, such as nitrogen and carbon dioxide, at a temperature in the range of from 150 to 600° C. for from 0.5 to 5 hours.

The catalyst composition of the invention finds especial use in the selective dealkylation of ethylbenzene.

The ethylbenzene feedstock most suitably originates directly from a reforming unit or naphtha pyrolysis unit or is the effluent of a xylene isomerisation unit. Such feedstock usually comprises $C_7$ to $C_9$ hydrocarbons, and in particular one or more of o-xylene, m-xylene, p-xylene, toluene, and benzene in addition to ethylbenzene. Generally the amount of ethylbenzene in the feedstock is in the range of from 0.1 to 50 wt % and the total xylene content is typically at least 20 wt %. Typically the xylenes will not be in a thermodynamic equilibrium, and the content of p-xylene will accordingly be lower than that of the other isomers.

The feedstock is contacted with the catalyst composition in the presence of hydrogen. This may be carried out in a fixed bed system, a moving bed system, or a fluidized bed system. Such systems may be operated continuously or in batch fashion. Preference is given to continuous operation in a fixed bed system. The catalyst may be used in one reactor or in several separate reactors in series or operated in a swing system to ensure continuous operation during catalyst change-out.

The process is suitably carried out at a temperature in the range of from 300 to 500° C., a pressure in the range of from 0.1 to 50 bar (10 to 5,000 kPa), using a liquid hourly space velocity of in the range of from 0.5 to 20 $h^{-1}$. A partial pressure of hydrogen in the range of from 0.05 to 30 bar (5 to 3,000 kPa) is generally used. The feed to hydrogen molar ratio is in the range of from 0.5 to 100, generally from 1 to 10 mol/mol.

The following Examples illustrate the present invention.

EXAMPLES

Example 1

The following matrix of silica to alumina ratios was obtained from the elemental analysis carried out by SEM/EDX by the procedures hereinbefore described on a ZSM-5 sample (Sample A) which was synthesized following the procedure of Iwayama et al in U.S. Pat. No. 4,511,547. Synthesis details such as crystallization temperature, time, etc. are given in Table 1 below, together with physical property data for the prepared sample. The ZSM-5 zeolite had an overall bulk silica to alumina ratio of 43.

The gray shaded area was used for the generation of a narrow slit line scan profile (by averaging the values vertically). The obtained profile is shown graphically in Figure 1.

Figure 1:
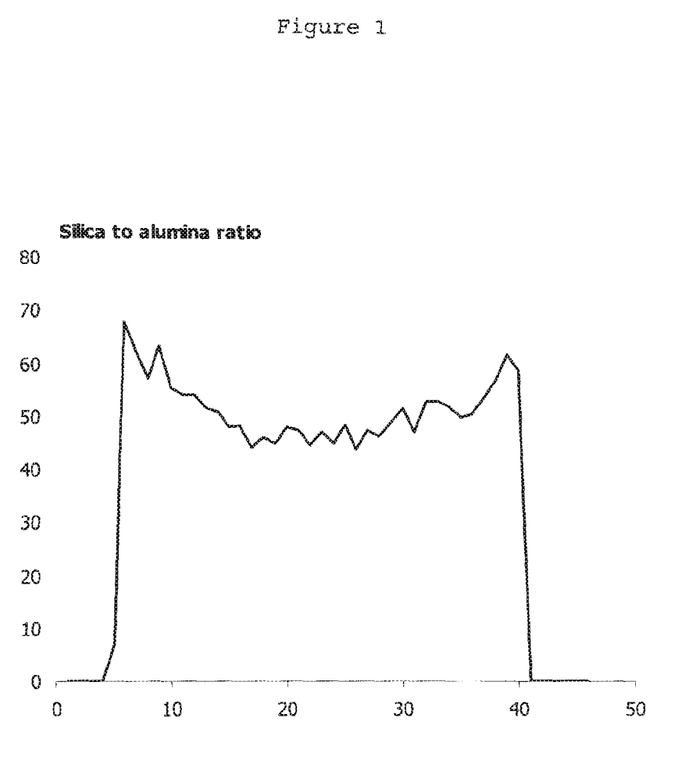
FIG. 1 is a graph of the narrow slit line profile of the silica-to-alumina ratio of ZSM-5 crystallite as determined by SEM/EDX analysis.

The sample shows a U shaped profile, where the silica to alumina ratio is higher at the edges of the crystallite than at the centre.

Example 2

In another synthesis, carried out analogously to Example 1, a new batch of ZSM-5 zeolite was prepared (Sample G). Synthesis and analysis details are given in the Table below. This zeolite also had an overall bulk silica to alumina ratio of 46.

Figure 2:
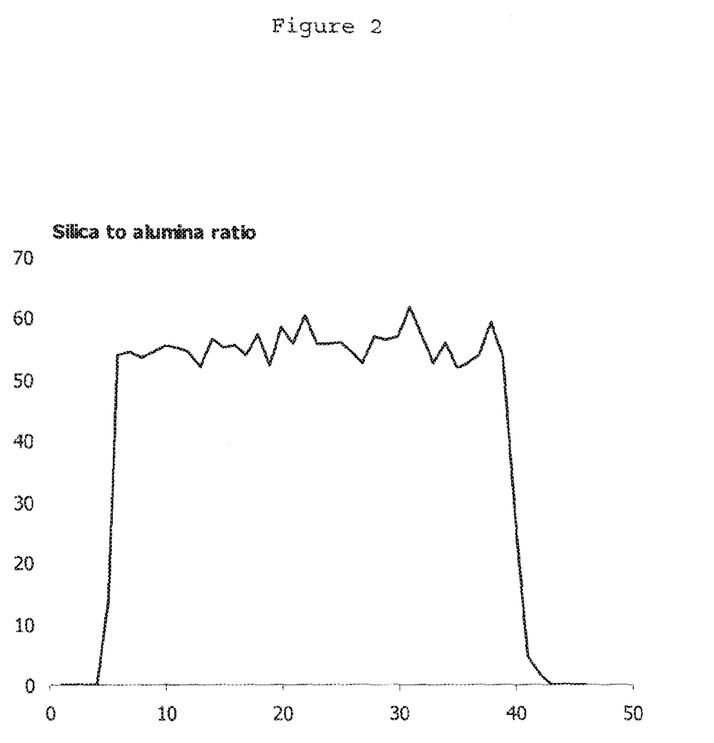
FIG. 2 is a graph of the narrow slit line profile of the silica-to-alumina ratio of ZSM-5 crystallite as determined by SEM/EDX analysis.

The obtained SAR map is shown below:

The narrow slit line scan profile obtained from the gray area is shown in Figure 2.

This sample shows a profile, where the silica to alumina ratio hardly changes from the edge to the centre of the crystallite.

Example 3

Additional ZSM-5 zeolite syntheses were performed following the Iwayama method as in Example 1, with slight variations in the crystallization temperature and the agitation speed. Table 1 below summarizes the synthesis conditions, the bulk analysis results, and provides additional information. Surface area was measured by the B.E.T. method.

TABLE 1

| Catalyst description | Sample A | Sample B | Sample C | Sample D | Sample E | Sample F | Sample G | Sample H |
|---|---|---|---|---|---|---|---|---|
| Crystallinity (% vs. ref.) | 109 | 105 | 95+* | 117 | 104 | 106 | 93+* | n.a. |
| SiO$_2$/Al$_2$O$_3$ | 43.1 | 43.2 | 44.6 | 44.1 | 42.5 | 41.7 | 46.2 | n.a. |
| Na$_2$O (%) | 0.01 | 0.01 | 0.01 | 0.01 | 0.02 | 0.05 | 0.03 | n.a. |
| Surface area (m$^2$ · g$^{-1}$) | 420 | 440 | 404 | 447 | 406 | 434 | 389 | n.a. |
| Autoclave scale (gal.) | 30 | 30 | 30 | 30 | 30 | 30 | 30 | n.a. |
| Tartaric acid source** | lab-L | lab-L | com-DL | com-DL | com-DL | com-L | com-L | com-L |
| Crytallization T (° C.) | 180 | 170 | 180 | 180 | 180 | 180 | 170 | 180 |
| Time at T (h) | 24 | 48 | 24 | 24 | 24 | 24 | 48 | 24 |
| Agitator speed (rpm) | 60 | 30 | 35 | 60 | 35 | 35 | 35 | n.a. |

*In these samples magadiite was found.
**lab-L: laboratory grade L-isomer, com-M: commercial grade mixed isomer, com-L: commercial grade L-isomer of tartaric acid.

Example 4

Catalysts were prepared from some of the zeolite samples prepared in Examples 1, 2 and 3 by mixing the ZSM-5 zeolite with silica as binder, extruding to form a shaped carrier, and then impregnating with hydrogenation metal by pore volume impregnation. Each carrier contained 40 wt % zeolite bound with silica (a mixture of Sipernat 50 from Degussa and Bindzil silica sol from EKA Chemicals in a weight ratio of 2:1). Each carrier was impregnated with a Pt/Sn solution so that the final catalyst had a composition of 0.02 wt % Pt and 0.4 wt % Sn.

The catalysts were subjected to a catalytic test that mimics typical industrial application conditions for ethylbenzene dealkylation. This activity test uses an industrial feed of European origin. The composition of the feed used here is summarized in Table 2.

TABLE 2

Composition of the feed used in the activity testing

| Feed composition | | |
|---|---|---|
| EB | wt % | 13.68 |
| pX | wt % | 0.18 |
| oX | wt % | 18.12 |
| mX | wt % | 62.06 |
| toluene | wt % | 0.48 |
| benzene | wt % | 0.13 |
| C$_7$-C$_8$-naphthenes | wt % | 5.35 |
| C$_9$+ aromatics | wt % | 0.00 |
| Total | wt % | 100.00 |
| C$_8$ aromatics | sum | 94.97 |
| EB in C$_8$ aromatics feed | wt % | 11.25 |
| pX in xylenes in feed | wt % | 0.22 |
| oX in xylenes in feed | wt % | 22.54 |
| mX in xylenes in feed | wt % | 77.23 |

The activity test is performed once the catalyst is in its reduced state, which is achieved by exposing the dried and calcined catalyst to atmospheric hydrogen (>99% purity) at 450° C. for 1 hour.

After reduction the reactor is pressurized without a cooling step, and the feed is introduced. This step contributes to enhanced catalyst aging, and therefore allows comparison of the catalytic performance at stable operation.

The catalytic datapoints are collected at a condition that exaggerates the potential negative operational effects. Therefore, the performance is measured not at the ideal industrial operating condition(s), but at those that allow a better differentiation of the various performance parameters used to evaluate catalysts in this application.

In the present case, a weight hourly space velocity of 4.6 h$^{-1}$, a hydrogen to feed ratio of 2.5 mol·mol$^{-1}$, a total system pressure of 1.3 MPa was used. The temperature was varied between 360 and 410° C. to achieve the required conversion for easier comparison.

The performance characteristics evaluated in this test are as follows:

$$EB \text{ conversion (wt \%)} = \frac{EB_{f.} - EB_{pr.}}{EB_{f.}} \times 100$$

$$\text{Xylene losses (wt \%)} = \frac{Xyl_{f.} - Xyl_{pr.}}{Xyl_{f.}} \times 100$$

where EB stands for ethylbenzene, Xyl for xylenes in general (all isomers), f for feed, and pr for product.

Example 5

Samples A, B, D, E, F, G and H prepared in Examples 1, 2 and 3 were analysed as described in Example 1 and 2. Typically 5 crystallites were selected randomly in the electron microscope, except for Sample B where only 3 crystallites were measured. These selected crystallites were subjected to the hereinbefore described X-ray mapping.

From the X-ray maps, the narrow slit line scan profiles were generated, and the slope of the profiles determined. These slopes were averaged per zeolite synthesis batch, and plotted against the xylene losses obtained in the test of Example 4 using the same zeolites in the catalysts.

The ratio of the average SARs (edge to centre) of the crystallites for each sample is given in Table 3 below and the plot of profile slope against xylene losses is shown in Figure 3.

TABLE 3

| Synthesis Sample | SAR ratio of the local averages at edges and centre |
|---|---|
| Sample A | 1.40 |
| Sample B | 1.17 |
| Sample D | 1.14 |
| Sample E | 1.06 |
| Sample F | 1.23 |
| Sample G | 1.08 |
| Sample H | 1.28 |

The most preferred materials are Sample A and Sample H in terms of having the lowest xylene losses.

An unexpected good correlation could be found between the slope of the silica to alumina distribution and the xylene losses at 65 wt % ethylbenzene conversion. This is to say that the steeper the profile, i.e. the larger the difference between the aluminium concentration between the centre and the edges of the zeolite crytallites, the lower the xylene losses in the ethylbenzene dealkylation process.

That which is claimed is:

1. An ethylbenzene dealkylation process, which process comprises: contacting, in the presence of hydrogen, a feedstock which comprises ethylbenzene with a catalyst composition, comprising ZSM-5 crystals, comprising a ZSM-5 crystallite having an average SAR at the edge of the crystallite and an average SAR at the centre of the crystallite, as determined via SEM/EDX or TEM/EDX elemental analysis, wherein the average SAR at the edge of the crystallite is higher than the average SAR at the centre of the crystallite.

2. An ethylbenzene dealkylation process as recited in claim 1, wherein the ZSM-5 crystallite has a ratio of the average SAR at the edge of each crystallite to the average SAR at the centre of the crystallite is at least 1.15.

3. An ethylbenzene dealkylation process as recited in claim 1, wherein the ratio is at most 3.

4. An ethylbenzene dealkylation process as recited in claim 1, wherein the slope of a second order polynomial fitted to the SAR values between the two edge SAR maxima, expressed as $-y'_0$, is at least 2.

5. An ethylbenzene dealkylation process as recited in claim 1, wherein the slope of a second order polynomial fitted to the SAR values between the two edge SAR maxima, expressed as $-y'_0$, is at most 6.

6. An ethylbenzene dealkylation process which comprises contacting, in the presence of hydrogen, a feedstock which comprises ethylbenzene with a catalyst composition, comprising: ZSM-5 crystals, comprising a ZSM-5 crystallite having an average SAR at the edge of the crystallite and an average SAR at the centre of the crystallite, as determined via SEM/EDX or TEM/EDX elemental analysis wherein the average SAR at the edge of the crystallite is higher than the average SAR at the centre of the crystallite; and a silica binder in an amount in the range of from 30 to 80 wt %, based on the total of ZSM-5.

7. An ethylbenzene dealkylation process as recited in claim 6, wherein the catalyst composition further comprises a hydrogenation metal selected from the group consisting of platinum, tin, lead, silver, copper, and nickel.

8. An ethylbenzene dealkylation process as recited in claim 7, wherein the total amount of ZSM-5 crystals present in the catalyst composition is in the range of from 20 to 50% based on the total carrier.

9. An ethylbenzene dealkylation process as recited in claim 8, wherein the catalyst carrier has been subjected to a dealumination treatment with ammonium hexafluorosilicate.

* * * * *